United States Patent [19]

Szabo et al.

[11] Patent Number: 5,066,496

[45] Date of Patent: Nov. 19, 1991

[54] COMPOSITION AND METHOD FOR TREATMENT OF GASTRIC AND DUODENAL ULCERS AND MUCOSAL EROSIONS

[75] Inventors: Sandor Szabo, Brookline, Mass.; Meryl S. A. Rubin, New Rochelle, N.Y.; Michael Klibaner, Brookline; Ahmad R. Kamarei, Lexington, both of Mass.; Robert S. Sinn, New York, N.Y.; Nicholas Catsimpoolas, Newton Ctr., Mass.

[73] Assignees: Angio-Medical Corporation, New York, N.Y.; Trustees of Boston University, Boston, Mass.

[21] Appl. No.: 227,739

[22] Filed: Aug. 3, 1988

[51] Int. Cl.$^5$ .................... A61K 35/30; A61K 35/12
[52] U.S. Cl. .................... 424/570; 424/574; 514/25; 514/925; 514/926; 514/927
[58] Field of Search .................... 424/95, 570, 574; 514/25, 925, 926, 927

[56] References Cited

U.S. PATENT DOCUMENTS 4,710,490 12/1987 Catsimpoolas et al. .............. 514/25

FOREIGN PATENT DOCUMENTS 0146810 7/1985 European Pat. Off. ............ 514/926
1057594 3/1986 Japan .................... 514/925

OTHER PUBLICATIONS

Cosolari et al. "Drugs cytoprotective for the gastric mucosa against alcohol agression" CA109:106330s.
"The Principles of Tetragonia Tetragonoides Having Anti-ulcerogenic Activity II. Isolation and Structure of Cerebrosides", Okuyama and Yamazaki Research Institute for Chemobiodynamics, Chiba Univ., Chiba, Japan, Chem. Pharm. Bull.; No. 7, pp. 2209 to 2219.

Primary Examiner—Jacqueline Stone
Assistant Examiner—Jean C. Witz
Attorney, Agent, or Firm—Felfe & Lynch

[57] ABSTRACT

Ganglioside mixtures and/or lipid mixtures e.g. from brain and omentum, are found to be effective to treat peptic ulcers.

6 Claims, 4 Drawing Sheets

Fig. 4.

| Lane | Description |
|---|---|
| 1 | BBG |
| 2 | Lp (First Chloroform Wash of Tup) |
| 3 | Lp (First Methylene Chloride Wash) |
| 4 (Plate) | Lp (Folch Ext. - C/M/W) |
| 5 (Plate) | Lp (Mc Ext. - Mc/M/W) |

TLC Conditions

Solvent: C/M/W (55:45:10)
 0.2% Each

Plate: Silica Gel

Sample Load: 2 and 3 (20 μm)
 4 and 5 (10 μm)

Dev. Reagent: Charring:
 50% $H_2SO_4$

Lane 1 bands: $GM_1$, $GD1a$, $GD1b$, $GT_1$

COMPOSITION AND METHOD FOR TREATMENT OF GASTRIC AND DUODENAL ULCERS AND MUCOSAL EROSIONS

SUMMARY

The invention concerns treatment of mucosal erosions e.g. gastric and duodenal ulcers with either omental extracts or ganglioside materials.

BRIEF DESCRIPTION OF THE DRAWINGS

FIG. 4 shows comparison by TLC of the method of the invention and that of Folch.

DESCRIPTION

Figure 1:
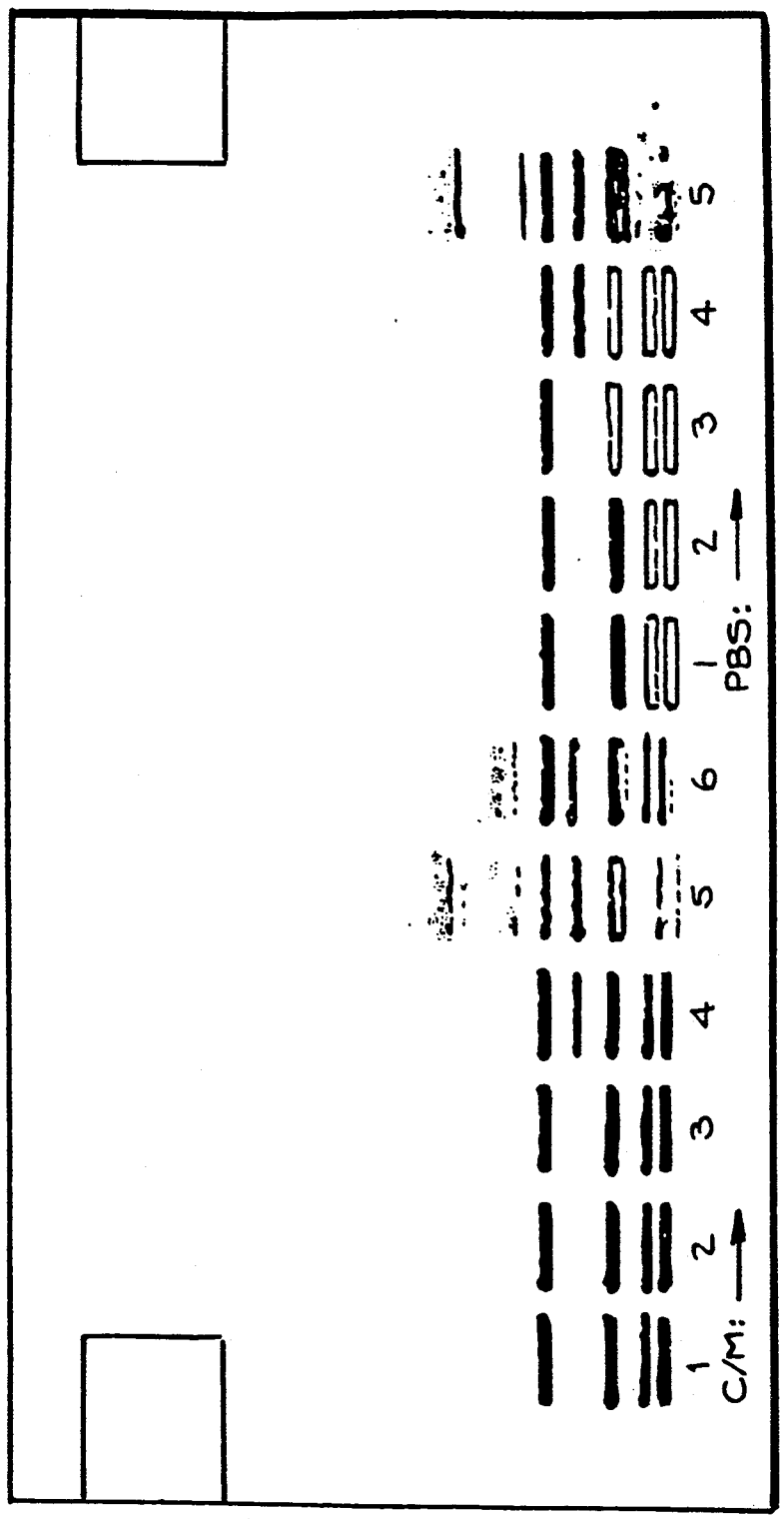
FIG. 1 shows a thin layer chromatogram (TLC) of bovine brain ganglioside (BBG) preparations.
Figure 2:
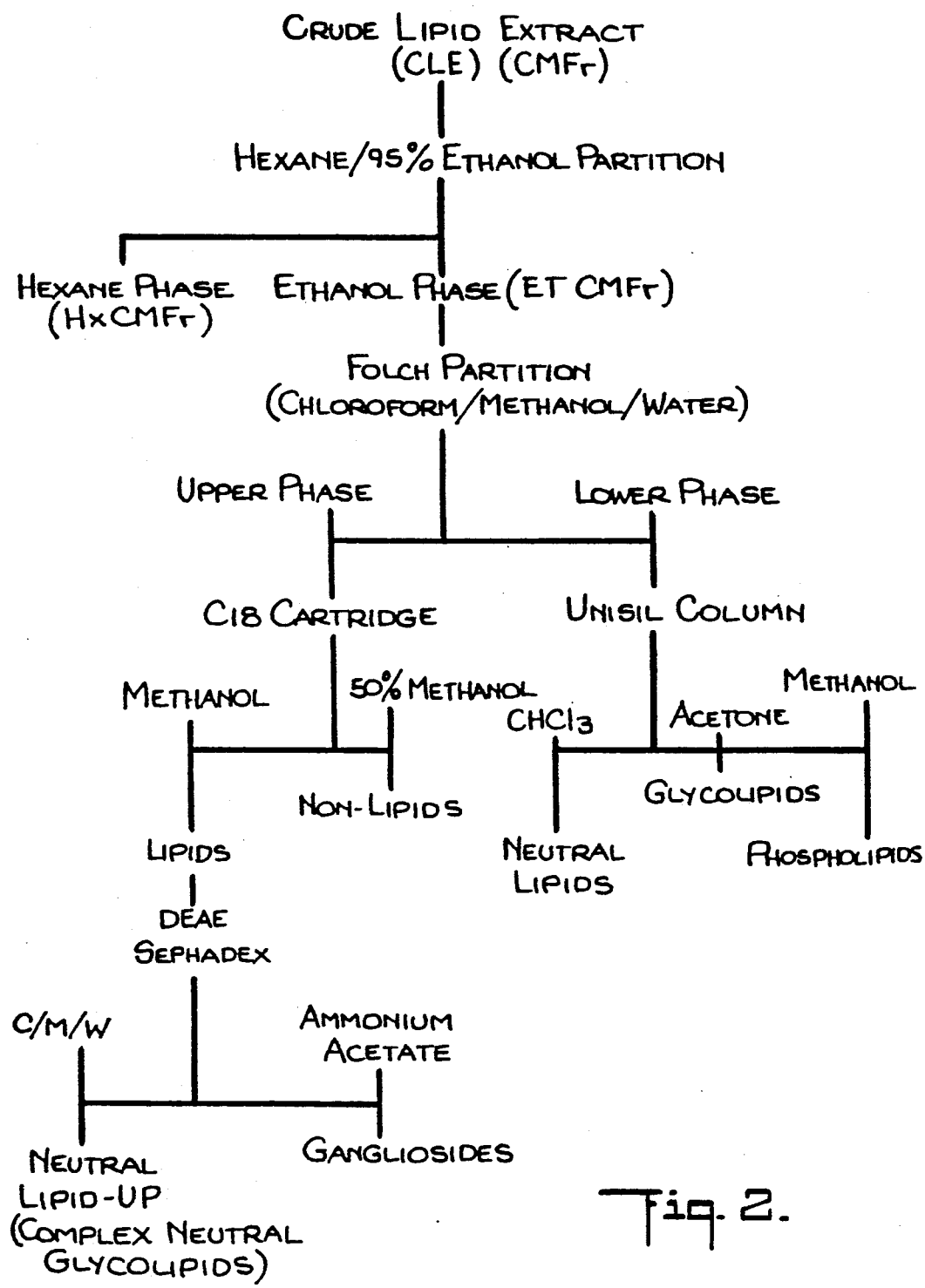
FIG. 2 shows fractionation of mammalian lipid omental material extracted by chloroform:methanol 2/1 (v/v) to show the various components any of which separately or together may contribute to the antiulcer effect.
Figure 3:
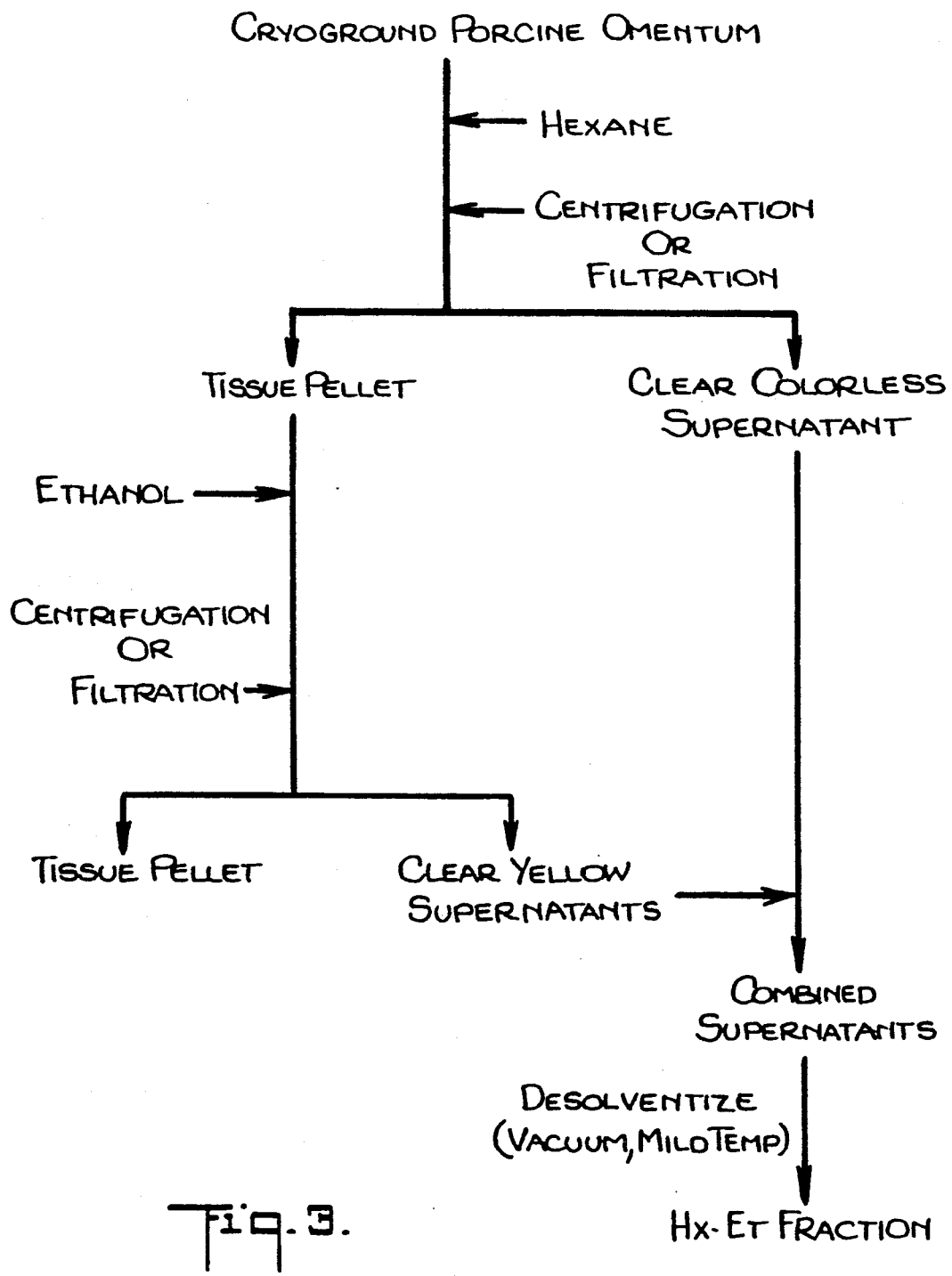
FIG. 3 shows hexane-ethanol sequential extraction of porcine omentum.

Peptic ulcers, which includes duodenal, gastric, channel postbulbar, marginal or stomal ulcers, jejeunal or stress ulcers have been treated for a long time by pharmaceutical agents. Subsequent surgical removal of all or part of the stomach or intestine occurs commonly when pharmaceutical methods have failed or penetration, perforation, malignancy or hemorrhage occur. Current favored drugs for ulcer treatment are histamine ($H_2$) receptor blocking agents such as cimetidine. Cimetidine competitively inhibits histamine binding at $H_2$ receptors, thus blocking gastric acid secretion stimulated by histamine, gastric parasympathetic activity and food. It decreases both basal and nocturnal gastric acid secretion, and reduces pepsin, intrinsic factor, secretion and gastric juice volume. In general, $H_2$ antagonists have an imidazole ring with some longer, more complex sidechain than the ethylenediamine side chain of histamine.

Other pharmacological agents which have been used in the treatment of peptic ulcers include sucralfate, a sucrose and aluminum containing disaccharide, and sulpiride, reported to act on the hypothalmus to diminish gastric secretion. Bismuth compounds such as Zolimidine and colloidal bismuth subcitrate and perhaps Peptobismol TM are described and in use in Britain and Scandinavia. U.S. Pat. No. 4,153,685 issued May 8, 1979 to Serfonteen describes protein complexes with bismuth. Carbenoxolone has also been used to effect healing of gastric and duodenal ulcers but its side effects detract from its usefulness; and it is not used in the U.S.

Certain prostaglandins ($PGE_1$, $PGE_2$, PGA) and their 16,16-dimethyl analogs inhibit gastric HCl secretion stimulated by histamine, pentagastrin or food. However advantages over existing drugs have yet to be demonstrated.

Applicants note U.S. Pat. No. 3,932,463 issued Jan. 13, 1976 to Schaub et al. concerning 11-dioxy-13-dihydro-prostaglandin-9-ketals and U.S. Pat. No. 4,017,534 issued Apr. 12, 1977 to Schaub et al. concerning 16-fluoro-11-deoxy-13-dihydroprostaglandin wherein both patents show use of the compounds as gastric acid secretion inhibitors. Prostaglandin analogues of $PGE_1$, $PGE_2$, $PGA_1$ and $PGA_2$ are disclosed in U.S. Pat. No. 3,903,297 issued Sept. 2, 1975 to Andre Robert for prophylaxis and treatment of gastric hypersecretion, gastric and duodenal ulcers.

Applicants also note U.S. Pat. No. 4,530,837 issued July 23, 1985 to Charon which discloses peptide derivatives as antagonists of gastrin and histamine. U.S. Pat. No. 4,428,942 issued Jan. 31, 1984 discloses analogues of the tetradecapeptide somatostatin which inhibit secretion of gastrin; however the analogues appear to be inactive against gastrin secretion.

In Ann. Surg. 201:290(1985), Sakamoto, T., et al. study stress induced ulcers and show a lower ulcer index for pentagastrin combined with EGF (epidermal growth factor), which may be accounted for by the endogenous somatostatin content of their material.

U.S. Pat. No. 4,370,317 issued Jan. 25, 1983 to Jorgensen et al. discloses a polypeptide which may be useful for treatment of gastroduodenal ulcers by inhibition of pentagastrin stimulated gastric acid secretion.

According to this patent the frequently demonstrated side reactions of cimetidine include diarrhea, exanthema, elevation of liver enzymes and gynecomastia. Further, there is some disclosure relating to use of glycoside-hydrolase inhibitors of microbial origin.

Klagsbrun, M. and Shing, Y. W. in *Pediatr Res.* 19:916 (1985) obtained a growth factor similar to EGF human milk that appeared to reduce the incidence, number and severity of cysteamine-induced duodenal ulcers. This positive effect of EGF-type material is echoed in the article by Shove-Olsen, P. et al. in *Gastroenterology* 90:911 (1986) using synthetic human EGF-/urogastrone which healed chronic duodenal ulcers as well as cimetidine.

However the history shows no use of lipid materials, particularly, but not exclusively, omental material or ganglioside material for healing of ulcers. The present work shows this healing effect in mammals. The following examples are described in order to be illustrative but not limitative of the present invention and it is understood that other embodiments within the spirit and scope of the invention will suggest themselves to those skilled in the art.

The extraction of omental material wherein CMFr is the chloroform-methanol fraction is described in the U.S Pat. No. 4,699,788 issued Oct. 13, 1987. Further methodology is included in the U.S. patent application Ser. No. 4,710,490 issued Dec. 1, 1987 and U.S. Pat. application Ser. No. 852,444 now allowed. All the above are hereby incorporated by reference.

Methods for isolation of ganglioside mixtures and description (Table 1, FIG. 1, below).

Essentially, however, the many methods for obtaining gangliosides from animal tissue involve three main steps of varying complexity, extraction, isolation and purification. The most common and benchmark procedure is Folch partitioning of the total lipid extract (chloroform/methanol/water). Gangliosides partition into the upper methanol/water phase, and most of the neutral lipids into the lower phase. Folch-Pi, J. Lees, Sloane-Stanley, G. H., *J. Biol. Chem.* 226:497–509 (1957); Trams, E. and C. J. Lauter, *Biochemica et Biophysica Acta,* 60:350, (1962); Autilio, L. A. and W. T. Norton, *Journal of Neurochemistry,* 12:543 (1965); Tettamanti, G., et al. *Biochemica et Biophysica Acta.,* Vol. 296:160 (1973); Quarles, R. and J. Folch-Pi, *Journal of Neurochemistry,* 12:543 (1965); Svennerholm, L. and P. Fredman, *Biochemica et Biophysica Acta.,* 617:97 (1980); Nilsson, O. and L. Svennerholm, *Journal of Lipid Research,* 23:327 (1982).

Isolation and purification of gangliosides from the upper phase can proceed according to methods known in the art. Isolation and purification of gangliosides usually requires long, complex procedures and is performed for analytical purposes or on small quantities of starting tissue or lipid material because of the large volumes of organic solvent required.

Ganglioside isolation and purification may require other steps, including removal of other contaminating lipids, dialysis, chemical precipitation or chromatography on:

(1) Silica gel: Gray, G. M., *Biochemica et Biophysica Acta*, 144:511 (1967); McCluer, R. H. and J. E. Evans, *Journal of Lipid Research*, 14:611 (1973); Ando, S., et al., *Biochemica et Biophysica Acta.*, 424:98 (1976); Kawamura, N. and T. Taketomi, *J. Biochemistry*, 81:1217 (1977); Irwin, C. C. and L. N. Irwin, *Analytical biochemistry*, 94:335 (1979); Leskawa, K. E. et al., *Analytical Biochemistry*, 140:172 (1984);

(2) Reverse phase packings: Yamazaki, J., et al., *J. Biochemistry*, 86:803 (1979); Gross, S. K. and R. H. McCluer, *Analytical Biochemistry*, 102:429 (1980); Sonnino, S., et al. *J. of Lipid Research*, 25:620 (1984); Watanabe, K. and Y. Tomono, *Analytical Biochemistry*, 139:367 (1984); Sonnino. G., et al., *J. of Neuroscience Research*, 12:179 (1984);

(3) Ion-exchange packings: Ledeen, R. W. and R. K. Yu, *J. of Lipid Research*, 13:680 (1972); Momoi, T., et al., *Biochemica et Biophysica Acta.*, 441:488 (1976); Iwamosi, M. and Y. Nagai, *Biochemica et Biophysica Acta*, 528:257 (1978); Fredman, P., et al., *Biochemica et Biophysica Acta.*, 618:42 (1980); Suzuki, Y., et al., *Lipids*, 20: No. 9:588 (1985); Mansson, J. E., et al., *J. of Chromatography.*, 322:465 (1985); Smid, F., et al., *J. of Chromatography*, 377:69 (1986); Whalen, M., et al. *Lipids*, 21: No. 4 (1986);

(4) thin-layer: Eberlein, K. and G. Gercken, *J. of Chromatography*, 16:425 (1975); Ando. S., et al., *Analytical Biochemistry*, 89:437 (1978); Harth, S., et al., *Analytical Biochemistry*, 86:543 (1978); Randell, J. A. and C. A. Pennock, *J. of Chromatography*, 195:257 (1980); Hunter, G. D., et al., *J. of Neurochemistry*, 37 (4):1025 (1981); Sonnino, S. et al., *Analytical Biochemistry*, 128:104 (1983).

Usually, tissue is extracted with chloroform/methanol (2:1, 1:1 or 1:2) in a blender and the tissue residue removed by filtration. Aqueous salt solution (0.2 total volume) is added to the extract to effect phase separation. The lower-phase is backwashed repeatedly with theoretical upper phase (TUP, methanol-water) to increase ganglioside recovery and all the aqueous upperphases are combined and desalted on a C-18 reverse phase packed column. The column eluate is dried, resuspended and subjected to alkaline hydrolysis to destroy ester bonds of unwanted neutral and phospholipids. After desalting on C18, the material is applied to DEAE-Sephadex to separate neutral and acidic glycosphingolipids (gangliosides). The eluate containing gangliosides is again desalted on C-18, to remove ammonium salts, and the gangliosides eluted with methanol again brought to dryness and finally taken up in chloroform/methanol.

EXAMPLES 1-5

According to the invention, prior to extraction, animal tissues are cryoground after freezing them in liquid nitrogen (subject of our pending application Ser. No. 811,507 filed Dec. 20, 1985 abandoned in favor of continuation applied filed Jan. 26, 1988, Ser. No. 148, 127 now allowed).

Extraction

Extraction of gangliosides has been done via two methods:

1. Sequential Extraction, first of non-polar lipids and then of polar lipids (subject of our pending application Ser. No. 040,611 filed Apr. 21, 1987). Cryoground tissue is initially extracted by simple mixing with five volumes of a non-polar solvent such as hexane, methylene chloride, etc. The remaining residue is then re-extracted with five volumes of methylene chloride/methanol (2:1). However, some ganglioside may be extracted into the non-polar solvent, in the order hexane > chloroform > methylene chloride.

Table 1, examples 2, 3 and 5 and the corresponding lanes of FIG. 1 show the application of normal variations of the method to purification of gangliosides from bovine brain and porcine omentum.

2. Direct Extraction: Cryoground tissue is extracted by simple mixing with ten volumes of methylene chloride/methanol (2:1). The extract is filtered to remove particulate materials. Then, sufficient volume of 0.88% KCl aqueous solution is added to the filtered extract to constitute 20% of the total volume taking into account the original water content of the tissue. After mixing, two phases separate. The upper phase contains most of the gangliosides contaminated by phospolipids and some neutral lipids, while the lower phase a small proportion of the gangliosides and most of the neutral lipids.

The polar extract may also contain other materials, such as carbohydrates, amino acids, etc. which could be removed via methods known in the art in order to ensure a pure sample of polar lipids.

Then, the lower phase is backwashed with a fresh portion of upper phase (UP) (methanol/$H_2O$ 7/3 v/v) equal to the volume of the original upper phase. The new UP is collected.

The two upper phases are combined, an equal volume of methylene chloride is added and mixed well. The resulting upper phase is washed with the same volume of methylene chloride two to four times more. Methanol added to the mixture during these washings with methylene chloride facilitates partition into two phases, but may also leads to loss of the least polar gangliosides.

Examples 1 and 4 of table 1 and FIG. 1 relate to normal variations of the method used for ganglioside purification from bovine and porcine brain.

Ganglioside Isolation

The final upperphase is made 0.1M with KCl, introduced at a moderate rate to a C-18 (reverse-phase) column that has been washed already with methanol and water. The column is eluted with methanol/water (4:6) containing KCl 0.1M salt solution, then water, then acetonitrile and finally methanol. The methanol effluent contains gangliosides and is collected and evaporated to dryness yielding a white ganglioside powder with few contaminants.

Alternatively, gangliosides can also be isolated after only 1-3 backwashes (rather than 5-6) by reapplying the methanol effluent from the C-18 column to a column of propylamine (an anion-exchange resin) that has already been washed and conditioned with methanol. The propylamine column is eluted with methanol and then chloroform/methanol (1:1) to remove non-ganglioside lipids. Elution of the column with 2.8% NH₄OH in methanol yields a white powder of highly purified gangliosides. This ganglioside mixture may be dissolved in appropriate organic or aqueous solvents (e.g., buffers) and filtered-sterilized. Isolation of appreciable quantities of individual gnagliosides from the mixture can be achieved through column chromatography.

Ganglioside mixtures purified from sequential or direct extractions, and commercially available individual gangliosides and mixtures were compared by thin layer chromatography (TLC). Known amounts of material were applied to silica gel 60 precoated layers (EM Science), and chromatographed in chloroform/methanol/0.25% $CaCl_2$ (55/45/20).

Individual components were identified by comparison to the migration rates of commercial reference standards and the literature on bovine brain ganglioside patterns. Charring with $H_2SO_4$ was used to locate all organic compounds, and staining with resorcinol for acidic glycolipids and orcinol for neutral and acidic glycolipids; concentrations as % total stained were calculated by integration of UV and visible scanning densitometry (Table 1 and FIG. 1).

the relative ganglioside concentrations are $GD_{1a} > GM_1 > GD_3 > GM_3 > GT > GM_2$ and GQ.

Advantages of the methodology

1) Direct extraction represents a rapid, straightforward method comprising 3 steps: extraction, isolation and purification. These which can be applied in both small and large-scale, using cryogrinding of tissue to produce a homogenous powder allowing greater efficiency of extraction and therefore higher yield.

2) Gangliosides have a unique extraction and isolation problem as compared to other lipids. Cryogrinding combined with direct extraction with 10 vol solvent led to much higher yields than homogenization and extraction with 20 vol chloroform-methanol (2:1). The use of methylene chloride-methanol has never been described for isolation of gangliosides although it has been used for isolation of other lipids (Carlson, Clin. Chem. Acta. 149:89–93 (1985). It is much gentler and does not require alkaline hydrolysis to destroy contaminating neutral and phospholipids.

3) Methylene chloride is safer and more stable than chloroform.

TABLE 1

| | GANGLIOSIDE PURIFICATION: EXAMPLES 1 THROUGH 5 (FIG. 1) | | | | | |
|---|---|---|---|---|---|---|
| Example | 1 | 2 | 3 | 4 | 5 | Standards |
| Source | bovine brain | bovine brain | bovine brain | porcine brain | porcine omentum | Sigma −2375 |
| Preparation | cryopowder | cryopowder | cryopowder | cryopowder | hexane extract residue | |
| Amount, kg | 1 | 1 | 1 | 1 | 1 | |
| Extract by | direct MC | sequential MC; MC/CH₃OH | sequential hexane | direct MC | sequential MC | |
| Product yield, g | 1.3 | 1.2 | 0.96 | 1.0 | 0.055 | |
| Lane on FIG. 1. | 1 | 2 | 3 | 4 | 5 | 6 |
| | Gangliosides as % total material stained or charred in lane | | | | | |
| $GM_3$ | — | — | — | — | 13.8 | — |
| $GM_2$ (?) | 0.78 | 0.72 | 1.1 | 0.77 | 2.2 | — |
| $GM_1$ | 22.8 | 25.0 | 21.8 | 23.1 | 23.8 | 33.9 |
| $GD_3$ | — | — | — | 13.3 | 15.9 | — |
| $GD_{1a}$ | 35.7 | 36.0 | 38.3 | 33.3 | 37.0 | 37.1 |
| $GD_{1b}$ | 18.4 | 16.0 | 17.0 | 12.5 | — | 5.0 |
| GT | 21.9 | 21.0 | 21.0 | 16.5 | 7.0 | 3.6 |
| Total | 99.6 | 98.7 | 99.2 | 99.5 | 99.7 | 79.6 |
| | Gangliosides below detection level: | | | | | |
| | $GM_3$ | $GM_3$ | $GM_3$ | $GM_3$ | $GD_{1b}$ | |
| | $GD_3$ | $GD_3$ | $GD_3$ | | | |

Ganglioside mixtures that had been prepared without anion exchange chromatography on propylamine were subsequently chromatographed on propylamine. The composition of ganglioside mixtures reisolated by these methods were unaffected by the ion exchange chromatography.

Gangliosides from any cryoground (or otherwise prepared) animal tissue can be isolated by sequential or direct methylene/chloride/methanol extraction, repeated washing of the upper methanol phase with methylene chloride and C-18 reverse phase chromatography.

As maybe seen from the examples in Table 1 and FIG. 1, the chromatographic pattern of gangliosides from porcine omentum is quite different from that of bovine brain and somewhat more similar to that of porcine brain; both quaitative and quantitative differences are apparent. Components migrating near where $GD_{1a}$ is expected are detected as doublets or triplets, which may indicate different fatty acid or carbohydrate composition from the standards. $GD_{1b}$ is undetectable in the omental ganglioside pattern. In porcine omentum 4) $GM_1$, the least-polar major ganglioside, of brain, is lost into the methylene chloride phase of a methylene chloride-methanol extract less than into the chloroform phase of a chloroform-methanol extract. FIG. 4 shows that in comparison to methylene chloride, the Folch lower phase (lane 4) and/or first UP (lane 2) remove more gangliosides especially less polar gangliosides. This finding confirms the shortcomings of the Folch method as noted in Kawamura, Nariko and Taketomi, Tamotsu, J. Biochem. 81:1217–1225 (1977), see Page 1218.

Methods for Isolation of Lipid Mixtures

EXAMPLE 6

Sequential extraction

Once the tissue powder has been prepared, additional optional steps are available for further processing prior to extraction. One possible desirable step is the removal of water from the tissue sample. This may be done, e.g., by freeze-drying, or lyophilization.

The tissue powder is then extracted, for example with a non-polar solvent, such as hexane, supercritical $CO_2$, and so forth. The extraction may be performed in concert with one or more physical manipulations of the tissue, such as by agitation or percolation, and the process can take place at room temperature or at mildly elevated temperature e.g., 30°-40° C.

The neutral lipids in the non-polar solvent are separated from the remnant of the extracted tissue; the tissue remnant then is extracted with a polar solvent, such as ethanol, methanol, etc., to remove polar lipids.

The extracts can be separately dried, preferably but not necessarily, under vacuum and mildly elevated temperatures. The resulting polar and nonpolar lipid isolates can then be used in various formulations and combinations. A preferred method, however, is mixing both extracts and then removing the solvent.

One skilled in the art will recognize the applicability of the method described herein to any and all sequential extraction processes of cryoground tissue powders, combination of various organic solvents, SCF, and different profile of extractions (e.g., nonpolar solvents, moderately polar solvents, and highly polar solvents and/or vice versa).

The examples herein are for illustrative purposes and are not meant to limit the invention which is contemplated to include the sequential extraction of any animal and/or plant cryoground tissue powder with one or a plurality of the organic solvents, supercritical fluids, and any combination thereof.

In all these examples, following the general concept explained supra, omentum or brain powder was prepared by first submerging the pre-cooled pieces of tissue in liquid nitrogen until they became brittle, and cryogrinding in a pre-cooled grinding mill to yield a freeflowing fine tissue powder. The powder was equilibrated at the appropriate extraction temperature.

Sample 1

Five hundred grams of porcine omentum powder was mixed at room temperature with 10 vol hexane per wt omentum powder until a uniform pink slurry was obtained (10-15 min). The slurry was centrifuged (2000 rpm, 20 minutes, room temperature) to obtain a clear colorless supernatant and a pink pellet of extracted tissue. The supernatant was dried by rotary evaporation under vacuum at 37° C., producing a white omental neutral lipid material. The recovery of neutral lipids was 430 g or 86%.

The extracted tissue residue was then mixed at room temperature with 4 vol absolute ethanol to obtain a uniform slurry (10-15 min) and centrifuged (2000 rpm, 20 minutes, room temperature) to obtain a clear slightly yellowish supernatant and a yellow-brown pellet. The second supernatant was dried by rotary evaporation under vacuum at 37° C. yielding a yellow, pleasantsmelling omental polar material. The recovery of polar lipids was 0.5 g or 0.1%.

Sample 2

1 kilogram of porcine omentum powder was extracted with hexane as in example 1. The recovery of neutral lipids was 807.2 g or 81%. The extracted tissue residue was then mixed at room temperature with 10 vol absolute ethanol as in example 1. The recovery of polar lipids was 4.5 g or 0.45%.

Sample 3

One kg of porcine omentum powder was extracted with 10 vol hexane at room temperature as in example 1. The recovery of neutral lipids was 840.4 g or 84%. The residue was mixed at room temperature with 10 vol absolute ethanol and treated as in examples 1 and 2. The recovery of polar lipids was 4.4 g or 0.44%.

Sample 4

Five hundred grams of bovine omentum powder was extracted as in sample 1 with 10 vol hexane at room temperature. The slurry was yellowish, rather than pink. The first supernate was dried by rotary evaporation vacuum at 37° C. (with a 50° C. thermal shock at the end) yielding 453.3 g (91% recovery) of yellowish omental neutral lipid material. The tissue residue was then mixed at room temperature with 4 vol absolute ethanol until a uniform slurry was obtained (10-15 min), and treated as example 1. The recovery of polar lipids was 0.7 g or 0.14%.

Sample 5

One kilogram of bovine omentum powder was extracted at room temperature with 10 volumes hexane until a uniform yellowish slurry was obtained (10-15 minutes), and treated as in sample 4. The first supernate, containing neutral lipids, was clear and colorless and was dried by rotary evaporation under vacuum at 37° C. (with a 50° C. thermal shock at the end), yielding 799.2 g (80% recovery) of yellow omental neutral lipid containing material.

The brownish-yellow tissue residue pellet was then mixed for 10-15 min. at room temperature with 10 vol absolute ethanol until a uniform slurry, and centrifuged (2000 rpm, 5 minutes, room temperature) to yield a clear slightly yellowish supernatant and a yellow-brown pellet (residue). Drying of the supernate by rotary evaporation under vacuum at 37° C. yielded 7.3 g (0.73%) of yellow, pleasant-smelling omental polar lipid product.

Sample 6

One kilogram ovine omentum powder was extracted 10-15 min. at room temperature with 11 vol hexane to obtain a uniform slurry that was centrifuged as above to separate a clear colorless supernatant and a pellet. The supernate was dried by rotary evaporation under vacuum at 37° C., yielding 896.2 g (89% recovery) of white omental neutral lipid product. The tissue residue was then re-extracted for 10-15 min. at room temperature with 10 vol. absolute ethanol and centrifuged as above to obtain a clear slightly yellowish supernatant dried by rotary evaporation under vacuum at 37°-40° C. to yield 1.2 g (0.12% recovery) of yellow, pleasant-smelling omental polar lipid material. The yellow-brown pellet from the second extraction was discarded.

Sample 7

One kilogram of porcine brain powder was extracted as for example 6 with 15 vol. hexane, and the extract dried by rotary evaporation under vacuum at 37° C. to yield 61.6 g (6.2% recovery) of white brain neutral lipid product. The extracted tissue residue was then mixed at room temperature for 10-15 min. with 10 vol. chloroform/methanol 2:1 and the slurry separated and filtered through Whatman #4 to obtain a slightly yellowish supernatant. The pellet (residue) was discarded. The supernate was dried as above to yield 27.3 g (2.7% recovery) of yellow paste-like brain polar lipid product.

Sample 8

Two hundred grams of cryoground cod liver powder was mixed (agitated) 10–15 min. at room temperature with 11 vol hexane. The slurry was centrifuged (2000 rpm, several minutes, 15° C.) to obtain a cloudy supernatant and a pellet of extracted tissue. The cloudy supernate was filtered, and dried by rotary evaporation under vacuum at 37° C. The recovery of liver neutral lipids was 91.9 g or 46%. The extracted tissue was then mixed 10–15 min. at room temperature with 10 vol. 95% ethanol (V/W) and the slurry centrifuged (2000 rpm, 15 min., room temperature) to obtain a transparent yellow supernatant and a pellet (residue). This yellow supernate was dried by rotary evaporation under vacuum at 37°–40° C. until no ethanol (or water) condensation was observed. The recovery of yellow polar lipids from cod liver was 9.8 g or 4.9%.

Sample 9

The material as prepared in this example was used as POE for the ulcer studies described below.

One kilogram of cold porcine omentum powder was mixed with 10 vol hexane until a uniform pink slurry was obtained (10–15 minutes); the slurry was centrifuged (2000 rpm, 5 minutes, room temperature) to obtain a clear colorless supernatant and 209.7 g of pink extracted tissue pellet. The pellet was re-extracted with 10 vol absolute ethanol to obtain a uniform slurry that was vacuum filtered (Whatman #4) to yield a clear yellow solution and a brown residue. First and second supernates were combined and dried at 37° C. until evaporation was nearly complete when the temperature was increased to 55° C. The final total lipid extract was yellow in color, had a pleasant sweet smell, and weighed 772.6 g (77.3% recovery).

Sample 10

One kilogram of cold porcine omentum powder was mixed with 10 vol hexane as for sample 9, yielding a clear colorless supernatant and 201.4 g pink extracted tissue pellet. The pellet was re-extracted with 10 vol. absolute ethanol, and slurry was vacuum filtered (Whatman #4) to obtain a clear yellow solution and a brown pellet. The two supernates were combined and dried as for sample 9, yielding 744.78 (74.5% of yellow), sweet-smelling total lipid extract.

To one skilled in the art, it will be apparent upon reviewing this disclosure that any type of tissue which contains lipid molecules may be extracted in the fashion described herein. Some of the tissue types which can be extracted and are derived from animal sources are nerve, muscle, adipose, cartilagineous, glandular, epithelial, endothelial, myocardial, circulatory, lymphatic, respiratory, digestive, skeletal, sensory and urinary tissue.

EXAMPLE 7

Effect of BBG and POE on Gastric and Duodenal Ulcer

These investigations assessed the effects of bovine brain gangliosides (BBG) and porcine omentum extract (POE) on development of pathology in animal models of gastric and duodenal ulcers, to establish whether these compositions can prevent the acute chemically induced gastric erosions, and whether they may accelerate the healing of chronic duodenal ulcers produced by cysteamine in the rat.

Study design—The experiments were performed in female Sprague-Dawley rats with an initial body weight of 160–200 g. Animals were housed in raised mesh-bottom cages over compacted dry animal litter in a room illuminated by standardized artificial light and maintained, unless otherwise stated, on Purina Lab Chow and tap water ad libitum. Every group (control and experimental) consisted of 3–5 rats. Each experiment was repeated at least twice and the results were pooled and analyzed for statistical significance by nonparametric tests or the two tailed Student's t-test for unpaired comparisons.

Acute hemorrhagic gastric mucosal lesions were induced by the administration of 1 ml of 100% ethanol or 0.6N HCl by gavage with a rubber stomach tube or by aspirin suspension (10 mg/100 g) per os (p.o.). After the initial dose-response studies using the ethanol model, 10 and 100 mg BBG per 100 g animal body weight (2% solution in saline) or 100 mg POE per 100 g body wt. (solubilized in mineral oil) was administered by gavage 30 min. before the ulcerogenic agent (ethanol, HCl or acidified aspirin) (Tables 2–4). Rats were killed 1 hr after the ulcerogen and the extent of gastric hemorrhagic erosions and ulcers were measured by computerized planimetry coupled with stereomicroscopy.

Duodenal ulcers were induced by cysteamine-HCl (Szabo, S., (1978) Am. J. Pathol. 93:273–276; Poulsen, S. S., et al. (1985) Dig. Dis. Sci. 30:161–167), 28 mg/100 g p.o. three times with 3–4 hr intervals.

In the acute duodenal ulcer models, the administration of cysteamine was preceeded by the potentially protective compounds p.o. (Table 5). The animals were killed on the third day, and the duodenal ulcers were evaluated as described below (see "At autopsy").

In the chronic duodenal ulcer model, cysteamine was administered as in the acute studies. On the third day after cysteamine administration, laparotomy was performed in each animal under ether anesthesia and the severity of the duodenal ulcer evaluated to create an almost equal and homogenous group of ulcers: rats with deep but not perforated ulcer visible from the serosal surface and penetrated ulcers (with liver or pancreas attached to the anterior wall of duodenum) were separated into control and experimental groups, while rats with normal serosa (presumably normal mucosa or superficial erosion) were eliminated. After creating control and experimental groups with about equal number of animals, on the third day, experimental animals were given the test compounds in two daily doses p.o. by gavage. Clinical examination of the animals was conducted daily and autopsy of dead animals was also performed daily. Surviving animals were killed 3 weeks after induction of duodenal ulcers by cysteamine.

At autopsy, duodenal ulcers were measured in the two largest diameters (mm) and at least 2 sections from the duodenum and 3 sections from the glandular stomach were fixed in buffered formaldehyde. Paraffin-embedded sections were stained with hematoxylin and eosin, and the periodic acid-Schiff technique for light microscopic evaluation of ulcer healing, connective tissue formation and degree of re-epithelization.

Results—10 mg/100 g of BBG or 100 mg/100 g of POE was administered by gavage 30 min before ethanol, HCl or acidified aspirin to chemically induce acute haemorrhagic gastric erosions. BBG and POE differentially affected the erosions. BBG was more protective than POE, while the vehicle mineral oil never exerted any protection.

The alcohol-induced gastric erosions were significantly decreased only by BBG, although POE also revealed some gastroprotective action against ethanol (Table 2). The similar appearing gastric mucosal lesions produced by HCl were significantly prevented by both POE and BBG, the latter almost abolishing the injury (Table 3).

Aspirin-induced hemorrhagic erosions usually involve 0.5-1% of the glandular stomach surface. The more than 50% decrease by POE in these lesions did not reach statistical significance, whereas the slightly more prominent protection by BBG was significant (Table 4).

Histologically, these chemically induced acute lesions were mainly hemorrhagic mucosal erosions combined with a few acute ulcers when the necrosis penetrated the muscularis mucosae. Severe congestion and edema, as well as focal hemorrhages, often involved both the mucosa and submucosa. Protection by BBG and POE was associated with absence of hemorrhagic erosions, congestion and hemorrhage, although mild edema and some superficial epithelial injury were still visible.

The acute duodenal ulcers induced by cysteamine were not influenced by either POE or BBG administered 30 min before the 3 ulcerogenic doses of cysteamine (Table 5). These lesions were mostly severe ulcers located on the anterior and posterior wall of proximal duodenum, very often with perforation or penetration into adjacent liver or pancreas. Localized or diffused peritonitis was also frequently seen and mortality in these groups was substantial.

The healing of chronic duodenal ulcers evaluated 3 weeks after induction by cysteamine was affected only by BBG which diminished the severity and size of duodenal ulcers (Table 6). BBG apparently accelerates the healing of chronic duodenal ulcers without influencing the development of acute duodenal ulcers. Actually, the incidence of chronic duodenal ulcers also showed a tendency toward decline in POE and BBG groups but the small difference was not statistically significant.

Prevention or reduction of microvascular injury, maintenance of mucosal blood flow or a slightly increased vascular permeability creating a histodilutional barrier in the gastric mucosa may be structural and functional targets of mucosal protection in anti-ulcer therapy. (Szabo, S., et al. (1987) J. Clin. Gastroenterol., 9, Suppl. 1, 8-13; Szabo, S., et al. (1986) Scan. J. Gastroenterol., 21, Suppl. 125, 92-96; Szabo, S. (1987) Scand. J. Gastroenterol., 22, Suppl. 127, 21-28; Szabo, S., et al. (1985) Gastroenterology 88, 228-236; Pihan, G., et al. (1986) Gastroenterology, 91, 1415-1426 and Dupuy, D., et al. (1988) Gastroenterology, 94, $A_{615}$.

The mechanism of antiulcer effect of BBG may not be the inhibition of gastric acid secretion since acute duodenal ulcer formation would have been influenced. Rather, it may be stimulation of cellular and tissue factors of healing (Brooks, F. P., et al. (1985) In: Peptic Ulcer Disease, Brooks, F. P., Cohen, S., Soloway, R. D., eds. New York, Churchill Livingstone, pp. 45-149; Szabo, S., (1984) Lab. Invest., 51:121-147; Gallagher, E. T., et al. (1984) Digestion 29:73-84.

Thus, experiments with BBG and POE in rats revealed that the acute gastric mucosal injury caused by ethanol, HCl or aspirin was significantly decreased by pretreatment with BBG, and was also affected by POE. These compounds appear not to affect the development of cysteamine-induced acute duodenal ulcers on a statistical basis but BBG appeared to accelerate the healing of chronic duodenal ulcers by decreasing the size of the ulcers. Thus gastroprotective and antiulcerogenic action of BBG and POE have been shown in this study. It will be apparant to those skilled in the art that other mucosal erosions in bowel conditions, disorders or diseases can be prevented or treated by BBG or POE; such as Irritable Bowel Syndrome or Irritable Bowel Disease (IBS or IBD).

TABLE 2

Effect of bovine brain gangliosides (BBG) and porcine omentum extract (POE) on ethanol-induced gastric erosions in the rat

| Group | Treatment+ | Area of mucosal lesions (% of glandular stomach) |
|---|---|---|
| 1 | Control | 12.8 ± 2.1 |
| 2 | Mineral oil | 13.6 ± 1.1 |
| 3 | POE | 8.4 ± 1.3 |
| 4 | BBG | 5.4 ± 1.9* |

+In addition, rats of all groups were given 1 ml of 100% ethanol by gavage, and animals were killed 1 hr later. BBG (10 mg/100 g) and POE (100 mg/100 g) were administered i.g., 30 min before ethanol.
N = 10 rats/group
*$p < 0.05$ vs. appropriate vehicle control.

TABLE 3

Effect of bovine brain gangliosides (BBG) and porcine omentum extract (POE) on gastric erosions induced by 0.6 N HCl in the rat

| Group | Treatment+ | Area of mucosal lesions (% of glandular stomach) |
|---|---|---|
| 1 | Control | 15.7 ± 2.0 |
| 2 | Mineral oil | 10.4 ± 1.6 |
| 3 | POE | 8.8 ± 1.4* |
| 4 | BBG | 2.9 ± 0.9** |

+In addition, rats of all groups were given 1 ml of 0.6 N HCl by gavage, and animals were killed 1 hour later. BBG (10 mg/100 g) and POE (100 mg/100 g) were administered i.g. 30 min before HCl.
N = 10 rats/group
*$p < 0.05$ vs. vehicle control.
**$p < 0.001$ vs. vehicle control.

TABLE 4

Effect of bovine brain gangliosides (BBG) and porcine omentum extract (POE) on gastric erosions induced by acidified aspirin in the rat

| Group | Treatment+ | Area of mucosal lesions (% of glandular stomach) |
|---|---|---|
| 1 | Control | 0.32 ± 0.10 |
| 2 | Mineral oil | 0.24 ± 0.09 |
| 3 | POE | 0.15 ± 0.07 |
| 4 | BBG | 0.12 ± 0.06* |

+In addition, rats of all groups were given aspirin (10 mg/100 g in 0.2 N HCl) by gavage, and animals were killed 1 hour later. BBG (10 mg/100 g) and POE (100 mg/100 g) were administered i.g. 30 min before aspirin.
N = 15 rats/group
*$p < 0.05$ vs. vehicle control.

TABLE 5

Effect of pretreatment with bovine brain gangliosides (BBG) and porcine omentum extract (POE) on acute experimental duodenal ulcer in the rat

| Group | Pre-treatment | Duodenal ulcer Severity (Scale: 0-3) | Size ($mm^2$) | Incidence (Pos./Tot.) | Mortality (%) |
|---|---|---|---|---|---|
| 1 | None | 2.7 ± 0.1 | 17.0 ± 3.7 | 10/10 | 40 |
| 2 | Mineral oil | 2.7 ± 0.2 | 20.4 ± 4.9 | 10/10 | 40 |
| 3 | POE | 2.4 ± 0.2 | 20.9 ± 6.6 | 10/10 | 50 |

TABLE 5-continued

Effect of pretreatment with bovine brain gangliosides (BBG) and porcine omentum extract (POE) on acute experimental duodenal ulcer in the rat

| Group | Pre-treatment | Duodenal ulcer Severity (Scale: 0-3) | Size (mm$^2$) | Incidence (Pos./Tot.) | Mortality (%) |
|---|---|---|---|---|---|
| 4 | BBG | 2.7 ± 0.2 | 23.4 ± 5.1 | 10/10 | 30 |

Pretreatment, POE (100 mg/100 g) or BBG (10 mg/100 g) were given by gavage 30 min before each of the 3 doses of cysteamine-HCl (28 mg/100 g, i.g.) on the first day. Survivors were killed on the third day after cysteamine.

Post./Tot. = positive rats with duodenal ulcer/total number of animals per group.

TABLE 6

Effect of pretreatment with bovine brain gangliosides (BBG) and porcine omental extract (POE) on the healing of chronic experimental duodenal ulcer in the rat.

| Group | + | Duodenal ulcer Severity (Scale: 0-3) | Size (mm$^2$) | Incidence (Pos./Tot.) | Mortality (%) |
|---|---|---|---|---|---|
| 1 | None | 2.0 ± 0.4 | 9.9 ± 3.3 | 8/9 | 22 |
| 2 | Mineral Oil | 2.3 ± 0.5 | 9.8 ± 4.4 | 6/7 | 0 |
| 3 | POE | 1.7 ± 0.4 | 12.4 ± 5.2 | 9/13 | 31 |
| 4 | BBG | 1.3 ± 0.3 | 3.6 ± 1.2* | 9/13 | 0 |

+In addition groups were given 3 doses of cysteamine-HCl (28 mg/100 the first day. On the third day, the animals were lapar, ether anesthesia, and those with no or superficiaions) (Scales 0 and 1) were eliminated, while those with (Scales 2 and 3) were used to homogenously form Groupent with mineral oil, POE (100 mg/100 g) or BBG (10 mg given by gavage once on the third day, and twice daily until the end of the experiment.
Autopsy on the 21st day when the survivors were killed. Mortality initiation of treatment (i.e., after third day).
Pos./Tot. rats with duodenal ulcer/total number of animals per group.
*p < 0.05 vs. vehicle control.

What is claimed:

1. Method for reducing incidence and severity of gastric ulcers caused by aspirin compromising administering to a subject susceptible to aspirin caused ulcers an amount of a pharmaceutically acceptable mixture of bovine brain gangliosides sufficient to reduce incidence and severity of said aspirin caused ulcers from forming.

2. Method of claim 1, wherein said mixture of gangliosides is administered orally.

3. Method of claim 1, wherein said mixture of bovine brain gangliosides is administered in an amount of about 10 mg per 100 grams of body weight.

4. Method for reducing incidence and severity of duodenal ulcers comprising administering to a subject susceptible to HCl caused ulcers an amount of a pharmaceutically acceptable mixture of bovine brain gangliosides sufficient to reduce incidence and severity of dudodenal ulcers.

5. Method of claim 4, wherein said mixture of bovine brain gangliosides is administered in an amount equal to 10 mg per 100 grams of body weight.

6. Method for reducing incidence and severity of gastric ulcers caused by aspirin comprising administering to a subject susceptible to aspirin caused ulcers an amount of a pharmaceutically acceptable, lipid containing porcine omental extract sufficient to reduce incidence and severity of said HCl caused ulcers.

* * * * *